United States Patent [19]

Gereg

[11] Patent Number: 4,498,473
[45] Date of Patent: Feb. 12, 1985

[54] VARIABLE STIFFNESS TRACHEAL TUBE

[76] Inventor: Gordon A. Gereg, 159 Saw Pit Hill Rd., Woodbury, Conn. 06798

[21] Appl. No.: 432,568

[22] Filed: Dec. 7, 1982

[51] Int. Cl.³ .............................................. A61M 25/00
[52] U.S. Cl. .................. 128/207.15; 604/96; 604/282
[58] Field of Search .................. 128/207.15; 604/96–104, 280, 282

[56] References Cited

U.S. PATENT DOCUMENTS

| | | | |
|---|---|---|---|
| 2,548,602 | 4/1951 | Greenburg | 604/96 X |
| 3,034,510 | 5/1962 | Kittel | 604/101 |
| 3,363,629 | 1/1968 | Kuhn | 128/207.15 |
| 4,248,234 | 2/1981 | Assenza et al. | 604/282 X |
| 4,336,798 | 6/1982 | Beran | 128/911 X |

Primary Examiner—Dalton L. Truluck

[57] ABSTRACT

A balloon type catheter or endotracheal tube is provided that can be inflated with a high pressure along part of its length so that it may be stiffened for easy insertion into the body. When in place in the body the air pressure can be released making the tube much more flexible but resistant to kinking due to a spiral wound plastic tube in the wall.

4 Claims, 2 Drawing Figures

VARIABLE STIFFNESS TRACHEAL TUBE

FIELD

Surgery, Cannula

This invention relates to a catheter or tube for insertion into the trachea of a patient by way of the mouth or nose for introduction of breathing gases during a period of anesthesia or respiratory treatment. The tube is made with a thin wall, often of polyvinyl chloride plastic, with a small hole or lumen running in the wall of the tube. A sealing cuff is bonded near the patient end to effect a seal in the trachea by pressurizing the cuff into contact with the tracheal wall. The pressure for the cuff comes by way of the small lumen that has connected to its other end an extending tube, often with a pressure indicating balloon and a valve means for inflating.

It is necessary to have the tube rather stiff so it can be guided into position by the clinician who can only hold one end of the tube as the other is within the body. Normally a device called a laryngoscope that is a strong metal guide that can be used to straighten the path from the mouth to the trachea is used in placing the tube. A light is usually on the patient end and various curls are included to help hold the tracheal tube on course. The tracheal tube itself has a beveled end also to make insertion easier. Some users insert a stiff wire or stylet into the tube so it may be shaped for easier insertion.

A shape has been developed and used as a standard that is a smooth arc of 14 centimeters radius. This arc is an average fit for most adults for either nasal or oral intubation and has been in use many years. The problem with the standard curvature is that the trachea is essentially straight and once the tube is in place it would be better if it were straight or shaped like an S to avoid having the tip of the tube forced against one side of the trachea or larynx. Pressurizing the sealing cuff adds to the problem by pushing the tip tightly to the side particularly if the trachea is not round, which it usually is not. As the breathing gas is forced into the lungs and withdrawn, the cycling of pressure on the lung side of the sealing cuff causes the tube to move axially back and forth. This movement causes the tip of the tube to damage the tracheal wall if it does contact it. There is also an equal and opposite force applied by the tube above the sealing cuff at the larynx which also can cause damage.

Several solutions have been offered for the problem with various degrees of success. Tubes are offered that have the standard curvature only up to the cuff and below the cuff (on the lung side) they are straight. This makes the tube harder to install but reduces damage. Very flexible tubes having a spiral wire core to prevent kinking work well if installed with a stylet. There is concern that the wire could be made to poke out of the assembly after some time of use.

A tip of much softer material helps reduce damage at the expense of possible occlusion as the tip is pushed aganst the trachea. Bigger, softer cuffs to help center the tube have also been tried with some success.

What is proposed in the present invention is a tube that can be made as stiff as a normal PVC tube with the standard curvature and having a normal patient end tip with a sealing cuff. In the stiff state the tube would be placed in the patient's trachea and the cuff inflated. The tube could then be changed to a very flexible state that would not exert undue pressure at any point. To effect the change would only require releasing air from a chamber in the tube wall, the stiffness coming from the air chamber being made rigid by air pressure.

Present tubes are a compromise of providing stiffness for insertion that is more than desired once the tube is in place. The present invention could make the tubes stiffer than common tubes when being inserted and much more flexible when in place. It would even be possible to select the stiffness desired by varying the air pressure applied. Using liquid instead of air would increase the possible stiffness and also give more weight to the tube.

These and other object of the invention will become more obvious from the following drawings and description where the numbers refer to like numbered elements.

Figures 1, 2:
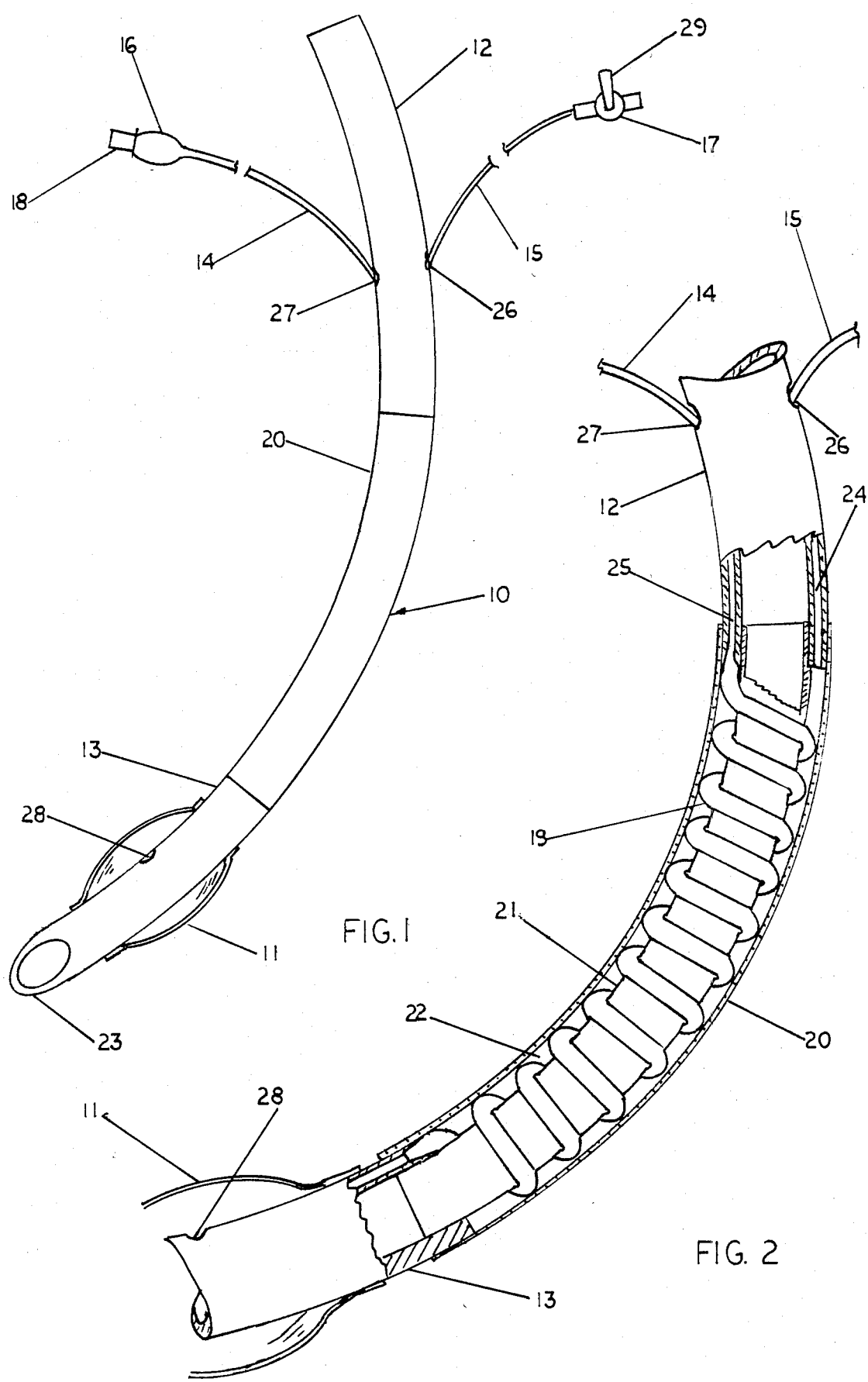
FIG. 1 is a side elevation of an assembled tube.
FIG. 2 is an enlarged side elevation in partial section of the center segment of a tube assembly.

In FIG. 1 a complete tube referenced generally as 10 is shown. Starting from the end of the tube 10 which would connect to a breathing machine, tubing 12 would appear to be normal tubing commonly used in endotracheal tubes except it would have two small passageways or lumens in its outer wall shown as 24 and 25 in FIG. 2 instead of the normal one. Extending tubes 14 and 15 fit into these lumens through notches 26 and 27 in tubing 12. A short distance from the notches 26 and 27, tubing 12 ends in a junction with a thin walled tube 20 having an outer diameter the same as tubing 12 and joined by being stretched over it into an interference fit and bonded by suitable means such as gluing or heat sealing. Tube 20 is flexible and covers a helical or spiral winding of small diameter tubing 19 which is itself wound on another smaller thin walled tube 21. Tubing 19 is bonded to both tube 21 and tube 20. The outer diameter of tube 21 is bonded by suitable means to the inner diameter of tubing 12. The resulting wall of the helically wound body section is the same thickness as tubing 12 or tubing 13. At the patient end of tube assembly 10 a piece of tubing 13 having the same inner and outer diameters as tubing 12 with a single lumen in its outer wall is attached to tubes 20 and 21 in the same manner as tubing 12. A cuff of the type typical of endotracheal tubes is sealed onto tubing 13 in the common manner over a notch 28 cut into the small lumen in tubing 13. The patient end 23 of tubing 13 is bevel cut, sealed and polished in the manner common to endotracheal tubes.

An airway extension tube 14 is fitted through notch 27 into small lumen 25 and has a balloon indicator 16 at its opposite end with a valve means 18 installed. Tubing 19 is also installed into lumen 25 and continues on its helical path to its opposite terminus where it is installed in the same manner into the small lumen in tubing 13. In this way an air passage is established from valve 18 to notch 28.

An airway extension tube 15 is fitted through notch 26 into small lumen 24 which is open to the space bounded by tube 21, tube 20 and tubing 19. This space extends in a helix from tubing 12 to tubing 13. Airway extension tube 15 is also connected to valve 17 and is shown without an inflation indication balloon that could be used. A two way valve 17 having a means to connect to a pressurizing source and a movable stem 29 for pressure closure or release is shown. Many other types of valves are suitable such as an automatic check valve that would open and close upon insertion or removal of a syringe or other pressurizing means.

From outward appearances or dimensional analysis, tube 10 would appear about the same as a common endotracheal tube of the same size except it would have an additional airway extension tube with valve. Components such as tubing 13, inflation indicating balloon 16, or cuff 11 would be interchangeable with ordinary endotracheal tubes.

Tube assembly 10 would be made of materials compatible with its use in contact with the body and would be handled in the same manner as endotrachealtubes commonly in use that are normally cleaned and sterilized. All markings required by standard or preference would be included. All requirements of the standard for tracheal tubes as set by the American National Standards Institute (Z-79.1 and Z-79.5) would be met. All bonds would be smooth and leak tight with no deterioration expected in normal use.

To put the invention to use, the clinician would remove it from its package in a totally deflated state. With a syringe or other pressurizing means he would inflate the body space 22 to a high enough pressure to cause the tube assembly 10 to stiffen in much the way a fully inflated toy balloon is stiff where a deflated one is very flexible. With valve 17 closed, the tube 10 would be introduced into the patient and positioned. Sealing cuff 11 would be inflated and breathing gas connections made. At a convenient time valve 17 would be opened releasing the air pressure in space 22 rendering the tube assembly 10 flaccid and allowing it to conform to the anatomical shape of the patient's airway. Tubing 19, being a small bore tube preferably made from a high durometer plastic, would give sufficient support to keep the tube from kinking.

Tube 20 and tube 21 would be made of a flexible plastic, preferably PVC, as that is a readily accepted material for endotracheal tubes. Rubber, thermoplastic rubber or other materials could also be used. The thickness of both tube 20 and tube 21 would be sufficient to allow bonding, strong enough to withstand wear and tear yet thin enough to be flexible for good complaince to anatomy. Transparancy would be an advantage but not necessarily required. Since suction catheters or other tubes are frequently inserted into the bore of an endotracheal tube, a smooth, nonstick surface is needed. All the material requirements can be accomplished with materials known to those skilled in the art.

Because in the preferred embodiment the assembly 10 is made from separate tubes 12 and 13 at each end, it would be simple to have variations at the two ends to suit the different requirements. The machine end might be made of a plastic being more elastic or having more tack to ensure a connector would be easy to insert and stay secure. The patient end could be made softer or radio opaque. The manufacturing process could be made more efficient by allowing the separate assembly and test of the components before their complete assembly.

I claim:

1. A catheter comprising semirigid tubular proximal and distal ends interconnected by a flexible tubular intermediate portion, said intermediate portion further including an inner tube and an outer tube coaxially spaced from each other to form a lumen, said lumen having within it a small tube contacting the inner tube and outer tube and connecting the distal and proximal tubes providing an air passage between same and taking a helical path, said air passage continuing into both the proximal and distal end tubes through a lumen in the wall of each tube and exiting at a notch in the wall thereby connecting on the proximal end to an extending tube ending in a closure, said notch in the distal end being positioned under a thin walled cuff sealed to the distal tube, said lumen being closed after the notch under said cuff, said proximal tube having a second lumen in the wall also having a notch and an extending tube ending in a closure providing a connecting passage to the space between said outer and inner coaxial tubes and said helical wound tube, said space being an airtight helix by way of bonding.

2. A tube assembly as in claim 1 where the two end tubes are of different construction such as number of lumens in the wall, hardness, color, radio opacity, elasticity, tip or end form, curvature or other features that may be desirable in one or both ends.

3. A tube assembly as in claim 1 having high pressure air or fluid in a helical passage in the wall said pressure making the tube stiffer than could be expected from the materials of construction and which could be varied by pressurizing means or valving.

4. A tube assembly as in claim 1 having a sector made up of one thin walled tube inside another similar larger diameter tube said sector supported by a helical winding of tubing fitting between the inner and outer thin walled tubes.

* * * * *